(12) United States Patent
Hörmansdörfer

(10) Patent No.: US 7,942,086 B2
(45) Date of Patent: May 17, 2011

(54) HOBBLE TURNING METHOD AND PREFERRED APPLICATIONS FOR SAID METHOD

(76) Inventor: Gerd Hörmansdörfer, Burgdorf-Beinhorn (DE)

( * ) Notice: Subject to any disclaimer, the term of this patent is extended or adjusted under 35 U.S.C. 154(b) by 284 days.

(21) Appl. No.: 12/380,277

(22) Filed: Feb. 25, 2009

(65) Prior Publication Data
US 2009/0165611 A1 Jul. 2, 2009

Related U.S. Application Data

(60) Division of application No. 10/935,558, filed on Sep. 7, 2004, now Pat. No. 7,513,913, which is a continuation of application No. 09/605,261, filed on Jun. 28, 2000, now abandoned, which is a continuation-in-part of application No. PCT/EP98/08473, filed on Dec. 12, 1998, and a continuation-in-part of application No. PCT/EP00/05325, filed on Jun. 8, 2000.

(30) Foreign Application Priority Data

Dec. 29, 1997 (DE) .................................. 197 57 799
Jun. 8, 1999 (DE) .................................. 199 25 924

(51) Int. Cl.
*B23B 3/00* (2006.01)
*A61F 2/32* (2006.01)

(52) U.S. Cl. .......................... 82/1.11; 82/118; 623/22.31

(58) Field of Classification Search .................. 82/1.11, 82/118; 411/436, 437; 623/22.31, 22.21, 623/22.23; 470/18, 10; 700/186, 187, 190; 408/10, 13, 3, 8
See application file for complete search history.

(56) References Cited

U.S. PATENT DOCUMENTS

| 3,874,809 A | * | 4/1975 | Hahn et al. .................... 408/3 |
| 3,894,297 A | | 7/1975 | Mittelmeier et al. |
| 4,287,462 A | * | 9/1981 | Beck et al. .................... 144/400 |

(Continued)

FOREIGN PATENT DOCUMENTS

DE 25 15 106 7/1976
(Continued)

OTHER PUBLICATIONS

Bar G et al: "Software Zum Berechnen Und Konstruieren Von Gewinden Sowie Ihrer Werkzeuge", Werkstatt Und Betrieb, DE, Carl Hanser Verlag, Muenchen, vol. 122, No. 4, Apr. 1, 1989, pp. 189-291, XP000036681.

(Continued)

*Primary Examiner* — Will Fridie, Jr.
(74) *Attorney, Agent, or Firm* — Collard & Roe, P.C.

(57) ABSTRACT

A process for hobble lathing, and preferred process applications, for the cutting of workpieces with non-circular or discontinuous contours on programmable lathes. The use and combination of a special program e.g. of thread cycles and hobble values for the diameter and/or the longitudinal axis or the pitch, the angle of the spindle, in option of a reciprocal-step technique and interleaved machining sequences opens up virtually infinite possibilities. The preferred applications of the process allow special threads to be cut on screw-in bodies, e.g. screw-in artificial hip joint sockets and bone screws for example with neutral or virtually any angle of pitch or relief of the thread blade as well as e.g. internal and external contours on workpieces for circular wedge connections. A particularly beneficial hip joint socket is presented comprising so-called screw or threaded surfaces.

22 Claims, 11 Drawing Sheets

U.S. PATENT DOCUMENTS

| | | | |
|---|---|---|---|
| RE32,211 E * | 7/1986 | Jerue et al. | 82/1.2 |
| 4,715,859 A | 12/1987 | Schelhas et al. | |
| 4,795,469 A | 1/1989 | Oh | |
| 4,834,759 A | 5/1989 | Spotorno et al. | |
| 4,851,006 A | 7/1989 | Tuke | |
| 4,878,916 A | 11/1989 | Rhenter et al. | |
| 4,883,491 A | 11/1989 | Mallory et al. | |
| 4,894,064 A | 1/1990 | Imhof | |
| 4,919,677 A | 4/1990 | Stubmer | |
| 4,944,759 A | 7/1990 | Mallory et al. | |
| 4,997,447 A | 3/1991 | Shelley | |
| 5,147,407 A | 9/1992 | Tager | |
| 5,224,404 A | 7/1993 | Kono et al. | |
| 5,295,076 A * | 3/1994 | Gruener et al. | 700/187 |
| 5,443,520 A | 8/1995 | Zweymuller et al. | |
| 5,571,201 A | 11/1996 | Averill et al. | |
| 5,755,799 A | 5/1998 | Oehy et al. | |
| 5,997,578 A * | 12/1999 | Hormansdorfer | 411/412 |
| 6,146,425 A | 11/2000 | Hoermansdoerfer | |
| 6,187,050 B1 | 2/2001 | Khalili et al. | |
| 7,044,974 B2 | 5/2006 | Garber et al. | |
| 2008/0025819 A1 * | 1/2008 | Hormansdorfer | 411/411 |

FOREIGN PATENT DOCUMENTS

| | | |
|---|---|---|
| DE | 29 50 536 | 7/1981 |
| DE | 31 41 287 | 4/1983 |
| DE | 35 09 240 | 9/1986 |
| DE | 40 31 079 | 4/1992 |
| DE | G94 18 900 | 1/1995 |
| DE | 44 00 001 | 7/1995 |
| DE | 44 14 866 | 11/1995 |
| DE | 195 20 468 | 11/1996 |
| DE | 197 57 799 | 7/1999 |
| EP | 0 318 679 | 6/1989 |
| EP | 0 358 345 | 3/1990 |
| EP | 0 480 551 | 4/1992 |
| EP | 0 902 342 | 3/1999 |
| JP | 64-5175 | 1/1989 |
| WO | WO 97/39702 | 10/1997 |
| WO | WO 99/33416 | 7/1999 |

OTHER PUBLICATIONS

RMS-Report 2002, D. Müller and G. Byolin, Deformationsverhalten Unterschiedlicher Hüftgelenkpfannen Unter Radialer Belastung-The Deformation behaviour of different acetabular cup types under radial loading; p. 17.

Mathys AG Bettlach: RM Pressfit Pfanne, http://www.mathysmedical.com/index.php?id=788 ; visited Aug. 12, 2008; pp. 1-4.

DePuy ASR XL-Kopfsystem, Jul. 2005.

Form-, Material-und Modularität der Schraubpfannen; H. Effenbeger et al, pp. 49-50, Feb. 2009.

International Search Report in PCT/EP98/08473 dated Mar. 11, 2000.

International Search Report in PCT/EP00/05325 dated May 18, 1999.

Preliminary Examination Report in PCT/EP98/08473 dated Mar. 30, 2000.

Preliminary Examination Report in PCT/EP00/05325 dated Feb. 9, 2001.

German Search Report in DE 197 57 799.7 dated Sep. 23, 1998.

German Search Report in DE 199 25 924.0 dated May 31, 2000.

\* cited by examiner

HOBBLE TURNING METHOD AND PREFERRED APPLICATIONS FOR SAID METHOD

CROSS-REFERENCE TO RELATED APPLICATIONS

This application is a divisional application of U.S. application Ser. No. 10/935,558 filed on Sep. 7, 2004 now U.S. Pat. No. 7,513,913, which application is a continuation of U.S. application Ser. No. 09/605,261 filed Jun. 28, 2000 now abandoned, which is a continuation-in-part of PCT application No. PCT/EP98/08473 filed Dec. 12, 1998, which claims priority under 35 U.S.C. §119 of German Application No. DE 197 57 799.7 filed on Dec. 29, 1997, and which is a continuation-in-part of PCT application No. PCT/EP00/05325 filed Jun. 8, 2000, which claims priority under 35 U.S.C. §119 of German Application No. DE 199 25 924.4 filed on Jun. 8, 1999.

BACKGROUND OF THE INVENTION

1. Field of the Invention

This invention relates to a special method for the turning of workpieces and preferred applications of the method. The invention also concerns a screw-in type artificial hip joint socket designed for cement-less implantation in the human medical domain.

2. Description of the Related Art

The principle of conventional lathing is a method which has been known of for many years and is used for the cutting manufacture of workpieces, e.g. of wood, metal or plastic. In recent years, lathing technology has undergone rapid advance due to the introduction and continuous development of numerical controls. Thus, today it is absolutely no longer any problem to, for example, maintain a constant cutting rate along a surface contour. With a suitable program it is now relatively simple to produce even the most complex rotationally-symmetric geometries in very short machining times. Furthermore, machines of this type can be further upgraded by equipping them with tool drives because this allows even complex workpieces to be lathed and milled to form a finished product with a single clamping. Despite this, there are certain limitations in connection with certain geometrical shapes or because of the time required. It is for example a fact that lathing in general has considerably shorter machining times than does milling. In addition, turning yields better surface qualities. If as a result of the geometry of a workpiece it is only possible to employ milling techniques, it is unavoidable that either a considerably longer machining time is involved or that a less uniform surface has to be accepted. However, this notwithstanding, even milling techniques are subject to certain limitations as far as the geometry is concerned. Thus, for example any corner of a milled contour in the radial plane of the milling axis can never have a corner which is sharper than the radius of the milling tool used. And while it may be possible to produce sharper contours using techniques such as broaching, percussion and erosion, it is necessary to transfer the workpiece to a different machine for this end. In the case of erosion the time requirement is also extremely long. While it is also true that the cutting of non-circular contours has been possible for a number of years now using profiling turning devices available commercially, these devices are expensive and therefore require a corresponding scale of capital investment. Furthermore such machines can only be connected to the initially intended interface and are limited to the specified contour with two-dimensional non-circular geometry.

In the past there have been attempts to enable lathes to machine non-circular workpieces by fitting special mechanical modules. One machine of this type is proposed in the German publication DE 25 15 106. In addition to the very complex and very sensitive mechanical configuration, this machine has extremely limited possibilities which in turn are themselves limited to the generation of two-dimensional non-circular geometries.

The geometrical possibilities for non-circular machining can be expanded with respect to a tool which can be fitted to the lathe if for example the cutting drive can be controlled in a freely programmable fashion. A tool of this type is for example described in the German publication DE 35 09 240 A1. In this case piezoelectric or magnetostrictive actuators are used in order to achieve a dynamic shift of cutting relative to the workpiece using appropriate electronic controls. However, this technique only allows extremely small adjustments to be achieved. While it would be technically possible, for example, to use a magneto-dynamic system to achieve considerably larger control movements, these would as previously be limited to a single movement axis. In order to achieve specific three-dimensional discontinuous machining it would be necessary to add a second or possibly even a third orthogonally arranged movement unit to create a tool with complex directions of movement, whereby this would be of extremely complex design and demand highly sophisticated control electronics. To date a tool of this design is not yet available.

There are known other special turning lathes which have been developed for non-circular machining, for example, of pistons for internal combustion engines. Modern pistons have in fact a very slight oval cross section, generally elliptical, in order to compensate for anisotropic expansion during heating. Having said this, there is however only a very slight deviation from the circular shape, whereby the contour also has a very flowing shape. There are no jumps or extreme discontinuities present. This being the case, the constructional design of a machine with this capability does not represent any major difficulty. In principle it is sufficient to allow the tool to oscillate with a slight amplitude on the X-axis of the diameter whilst the carriage traverses the workpiece in the Z-axis. In so doing the path of the tip of the tool will follow a more or less sinusoidal curve such that extreme acceleration is not necessary. This latter would be very difficult to achieve despite the reduced mass of the system. It is pointed out that such machines require a coupling of the workpiece rotation to the movement along the x-axis whereas the advance in the Z-axis can be freely chosen. In fact the generation of the non-circular contour is restricted to the two-dimensional diameter plane and is only extended in a third dimension by way of the Z-axis. In reality the Z-axis is not actually involved in the generation of the non-circular contour. There is no technique for moving the carriage along the Z-axis in jumps or with superimposed oscillation, for example.

A special machine of the type described above is described in the German publication DE 40 31 079 A1, for example. In this case it is proposed to control the drive required for the oscillating movement of the tool (for example an electric linear motor or a hydraulic system) by means of an extra computer control in addition to the existing mechanical control, whereby this could be a personal computer, for example. However, a machine of this description would be limited in its possibilities to the intended and similar applications unless its basic kinematic method is modified. Furthermore, a special machine of this description would be relatively expensive to acquire.

SUMMARY OF THE INVENTION

Therefore, the task at hand was to create a method for lathing workpieces with irregular, discontinuous or abruptly changing contours which on the one hand makes use of the existing possibilities of a machine with compound slide and NC control, as well as in connection with additional equipment such as linear slides. On the other hand it should overcome inertial problems and at the same time provide the option of extending the degrees of freedom with respect to the discontinuity of the intended contour by at least one additional dimension. In so doing a further goal of the new method is to waive the need for the previously necessary milling operations as far as possible.

The task referred to is solved by the invention using a turning method which is described by the applicant as hobble turning (also referred to as jerk or limp turning). In this the workpiece is rotated in the chuck of the machine spindle at a preferably constant speed of rotation during which the compound slide with the optionally fixed or controllable cutting tool is moved along the chosen axis, e.g. the pitch axis using e.g. a thread program or a C-axis program synchronized to the spindle axle to generate specific non-circular contours made up of combinations of geometrical transitional elements using a program of jump functions by linking command blocks with values for selected address parameters e.g. diameter (X), length (Z) and either angle (C) or pitch (F) whereby for at least one of these parameters in the program block chain a sequence of hobble value groups is used with at least one numerical value in each value group. This method can be expanded by including the parameter height (Y) in suitably equipped machines.

In order to generate a specific tool track relative to the workpiece the over-shoot, the inertia, contouring error and the nominal all rigidity of the components concerned are all specifically exploited. However, it is in particular proposed to generate a tool track which only partially corresponds with the required discontinuous contour. It is then possible to either remove the non-required, or unusable sections or those sections non-compliant with the specifications in a follow-up machine cycle e.g. by milling, or to correct the contour to achieve the final contour using subsequent hobble machining. In the case of certain tasks it is especially advantageous to employ a jump system according to the invention in which the discontinuity to be created using interleaved sequential sequences comprising geometrically opposed staggered lathing cycles.

When programming the control according to the invention to generate the required tool movements in most processing tasks the increments formed between the numerical values for at least one address parameter in the program block chain represent a hobble sequence of value groups with at least one numerical value in each value group, whereby for example the corresponding numerical value within one value group is larger than that within the other and/or the sign within one value group is positive and within the other value group is negative. In principle the program values in the program block chain for a certain address parameter form a sequence of numerical values in which the commanded jump function is expressed as hobble steps. In so doing the respective target coordinates can be plotted as dots on a curve whereby they are connected by straight lines. It is part of the nature of the invention that in those sections of abrupt contour changes, in particular the tool track generated, will not to be compliant with the straight lines but will approximate the straight line in the form of rounded transitional functions.

The special significance of this method is its applicability in all three dimensions, even without the inclusion of the height axis (Y). This machining freedom is due to the fact that the hobble steps can be programmed via X, Z, F and C either singly or in combination with one another as well as in connection with a tool with linear drive.

In its simplest form the method according to the invention requires neither special equipment nor additional NC controls. It can be realized based solely on the use of the possibilities provided by the machine control and appropriate software and is only limited by the dynamics of the overall system. This can comprise for example the known command blocks G 01, G31, G 33, G 34, G 37 or G 131 etc., whereby for example address parameter diameter dimension (X), longitudinal dimension (Z), thread pitch (F), start-up length (B), overshoot length (P), start-up angle of the spindle (C), reference direction for F (H) and change in pitch (E) may be used or by inserting blocks with special software. The possibility is also not excluded that based on the method proposed here the industry will in the future offer expanded programming possibilities as standard.

When driven special tools are not utilized, the dynamics described above of the overall system is made up of the mechanical and electronic dynamics of the machine. The mechanical dynamics is dependent upon the mass of the compound seat and on the response speed of the drive, e.g. comprising threaded spindles, motors and gears. In contrast the electronic dynamics is dependent upon the speed of the control method and/or its links with the electrical motor drives. It is therefore the case that lathes of the latest generation equipped with digital drives and the fastest computers are suitable for extreme machining of ovality whereas the application of this method on older machines will have corresponding restrictions. These restrictions can to a certain extent be partially overcome by the use of reduced cutting speeds during lathing because this results in lower spindle speeds and also correspondingly reduces advance speeds.

A very simple application of this method comprises for example the lathing of eccentric journals. In this case for example an angular resolution of 180.degree. is realized with respect to the workpiece by, for example, linking command blocks, e.g. in this case G 33, by in each case programming the start-up co-ordinates in X and Z and a pitch in F whereby the increments lying between the programmed Z values of in each case 180.degree. for the angular step referred to must in principle have a value of half of the programmed pitch value. In contrast, the values for X for each 180.degree. half step vary backwards and forwards between a larger and a smaller programmed diameter value, whereby in theory the average value corresponds with the diameter of the journal and the half difference corresponds with the eccentricity of the journal. In order to simplify the programming work, it is possible for example to enter the repeating jump(s) in the Z or in the diameter axis in some controls as a variable. Since in the example described the diameter change is generally larger than the intended advance, in this case the pitch, in a normal case the machine control will deduct the programmed pitch against the advance on the X-axis. Therefore it is necessary that for the pitch, the value F—i.e. the path programmed with respect to the diameter per rotation—must be entered as double the diameter difference, unless the reset is prevented by command blocks, e.g. with H. The programming described produces a theoretical track curve of the compound seat having the form of an extending zigzag line. In effect, however, because of the various ameliorating factors, e.g. the high mass of the compound seat and the insufficient rigidity of the control loop, the movement of the compound seat during advance along the workpiece is actually a continuously repeated quasi-sinusoidal curve such that despite the in principle primitive programming a remarkable roundness of the eccentric journal is achieved. On the other hand this distortion means the measurable dimensions of the workpiece do not correspond exactly with the programmed values. It is therefore necessary to determine the actual programmed numerical values based on trial workpieces. Based on these it is, however, possible to reproduce the dimensions with high precision on the machine concerned.

The procedure described above is applicable for the turned production of elliptical bodies, in that the programmed zigzag curve is specified with a double resolution, i.e. with angular steps of 90.degree. In this case the two alternating program diameters describe the theoretically maximum and minimum diameters of the ellipse. It is then necessary to program the pitch which is usually calculated by the control along the X-axis with a value of four times the diameter difference.

A similar procedure is then adopted if it is intended to produce a polygon (a so-called orbiform curve) whereby the resolution of the angular step must be 60.degree. Machining of this type is for example interesting in the production of face-side cut grooves, as used today for example as the lubricating groove of starting discs or the cleaning groove of disk brakes. Proper functioning in these cases does not require precision machined groove tracks, such that any track deviations can be disregarded.

The examples described above are concerned with relatively harmonious non-circular items with a constant advance in the longitudinal axis with fixed and programmed pitch. It is easily possible to extend the programming described by the addition of auxiliary points in order to produce perfect contours. The method according to the invention can be extended considerably further because it enables extreme jump machining of the workpiece, also along the longitudinal axis.

To achieve this result it is proposed to use cutting techniques to produce workpieces with even greater in particular spatial discontinuities and with angular contours or to achieve higher degrees of track precision by bringing in variable or stepped pitch values, for example also in connection with a finer resolution of the contour. In the program the track to be followed by the compound seat in order to achieve a specific contour is described in the form of linked blocks, e.g. with G 33, with a different pitch specified in each program block whereby in extreme cases, e.g. a very small value for F followed in the next program block by a very large value for F results in for example a sequence of soft then abrupt movements of the compound seat. This method allows the lathing of discontinuities of great diversity to be achieved for example also the surface shell of curved bodies. It is possible in a similar fashion to use this method to achieve discontinuous contour outlines as described by using co-ordinate chains programmed in the program block made up of only respective X and Z values or also in connection with F values. Thus for example the advance in one or both axes can be programmed as reciprocal-steps whereby after a certain advance movement there follows an in each case abrupt (shorter) return jump which is in turn followed by for example a larger advance distance. In this sense such a method can for example be understood as being the alternating cutting of linked right and left hand threads with under certain circumstances asymmetrical thread pitches.

The method according to the invention also allows the cutting of discontinuous contour elements protruding from an angled or curved surface shell whereby the side of the tool predominantly works the flank of the discontinuous contour element and the tip of the tool predominantly cuts the surface shell. In this case suitable programming of start and finish points and pitch allows the tip of the tool to be controlled along a track which for the most part runs tangentially to the surface shell and the side of the tool generates the flank of the discontinuous element controlled by a programmed change of the travel speed and/or travel direction.

In the programming described particular care must be taken to ensure that the reference direction for F, which is generally described with address parameter H, is correctly used. As is known, H describes which axis is used to calculate the advance which corresponds with the thread pitch programmed under F. Without other specifications or where H=0, the advance refers to the Z-axis, i.e. in principle to longitudinally, conical and similarly linked threads up to maximum 450 to the Z-axis. If H=1 then the advance calculation now refers to the X-axis, i.e. to basically planar, conical and correspondingly linked threads of maximum 45.degree. degrees to the X-axis. In this case H=3 refers to movement on the thread track. In the case of linked threads on curved surfaces it can easily occur that the limit value of 45.degree. is exceeded and the machine control then automatically springs over to the other axis calculation. This must be either determined for example by conversion and be deliberately falsified in the program or this reset must be prevented by appropriate software in the event that the control system has such a command block available, e.g. with I for a face pitch and K for a I longitudinal pitch.

To complement this the programming of the target coordinates X and Z in connection with the pitch F using a command block for threads (e.g. G 33) has the problem that the actual pitch of zero will not be accepted by the control. One possibility of overcoming this obstacle is to set these parameters to the minimum programmable increment (e.g. 0.001 mm).

In the case of the invention, however, there is an even more elegant method to eliminate this problem whereby this also simultaneously avoid the reset at 45.degree. as well as reduces of the programming work. In this method the hobble program e.g. in command block G 01, is specified in the form of coordinate chains of X and Z, and the spindle angle C. This waives the need for calculation of the respective pitch because this is derived from the difference between the in each case selected reference parameters (Z or X) in relation to the spindle angle C. In the case where the angular steps between sequential spindle angles in the command blocks are the same or all repeat themselves within a specific regularity, e.g. as a hobble rhythm, then the value for C can be programmed as a variable. In this case the parameter is either raised or lowered in value, after completing of the respective program block, by an amount equal to the respective angular step value which can also be programmed as a variable or as a fixed value. In the event that changes are required to the, under certain circumstances extremely long, programs it is then generally possible to modify only a smaller number of fixed values or variables.

The method described above for spindle programming is however only suitable for certain machines and NC controls which are compliant with state-of-the-art developments. In these machines the spindle is integrated in the drive motor whereby the entire unit can be addressed either as the turning axis or as the C axis. With correspondingly fast NC controls there is a certain degree of a equivalence with respect to programming between the speed of turning of the spindle, which is for example expressed in that the C axis can be used even at very high rpm (under certain circumstances several thousand rpm). This means that the programming of the C axis allows cutting speeds to be achieved which are comparable with those of standard lathing operations.

The overall method according to the invention is further extended by the proposal to overcome application limitations due to the restrictions of machine dynamics or of the linear driven tool in that for extreme machining geometries an interleaving of the processing sequences is employed. This refers to a kind of jump method in which for example a first machining cycle produces a first contour element but which at the same time also skips a second in order then to follow a third contour element when its tracking has steadied, and so on. The contour elements missed out of the first machining cycle are then cut in a second machining cycle, whereby the contour elements of the first machining cycle are now skipped. This method takes into account that the overrun of the overall system as a result of an abrupt movement programmed at maximum traversing speed means that the overall system is not able to track a contour element which follows at a close distance and will not be traversed in the desired manner. Although in order to execute the method two or more machining cycles may be required, which takes longer, this nevertheless represents a drastically shorter time than that required by milling techniques.

Together with the invention preferred applications of the method are also proposed. These applications also serve to provide a more detailed explanation of the method based on a number of application examples.

The proposed application concerns the production of threads for diverse, in particular self-tapping screw-in bodies into yielding materials whereby such bodies are e.g. wood, plastic and bone screws including e.g. implants such as lag screws, vertebral fusion bodies, screws for fixateur externe, screw in posts for dental implants and artificial hip joint sockets.

A further application is the inexpensive manufacture of so-called circular wedge profiles on the internal or external coupling faces of coupling elements in mechanical engineering.

One of the above proposed applications refers preferentially to self-tapping artificial hip joint sockets for cement-free implantation into humans. These kinds of screw-in type artificial hip joint sockets are available commercially in various designs. In order to ensure reliable and permanent integration and also simplified handling during implantation surgery the design of the thread is of primary importance. It is known in the interim that a large contact area of the implant to the bearing surface without stress peaks and a threaded profile inclined towards the pole of the socket help create the best preconditions to avoid loosening. On the other hand, such a screw-in type artificial hip joint socket must provide good tactiliance, which is a term which describes the "feel" of the surgeon for the seating of the socket body on the prepared bone surface in the acetabulum during the screwing in of the screw-in type artificial hip joint socket. In existing screw-in type artificial hip joint socket types there is a need for improvement because they either leave undesirable free spaces to the bone interface after implantation or can only be screwed in with excessive force or their tactiliance is insufficient, i.e., the surgeon does not "feel" when the socket has seated in the bone.

One group of screw-in type artificial hip joint sockets is configured with a so-called flat screw in which the lateral surfaces of the thread rib are parallel to one another. It is standard procedure to interrupt the thread web by machining tapping groove(s) at certain intervals in order to form cutting edge(s). In this type of thread the cutting force during self-tapping must be applied totally via the radial head surface of the thread rib which is inclined outwards or by any cutting edge(s) which are in situ there. When these other measures are undertaken, however, the head surface of individual thread teeth describes a spiral curve in the axial view of the pole-side of the screw-in type artificial hip joint socket, the exact track of which is dependent on the form of the shell body of the screw-in type artificial hip joint socket and the pitch of the thread. As a result the radial curve spacing from the polar center increases with progressive turns. The end of any one thread tooth is therefore at a greater radial distance outwards than at its start. This means that during screw-in of such a screw-in type artificial hip joint socket a pinching effect is created which can only be ameliorated by the filing forces of the roughened surface of the implant on the bone material. This means that implants of this design have unnecessarily high screw-in forces.

On the other hand, screw-in type artificial hip joint sockets are available with a flat thread, the thread teeth of which have a relief angle created by over-milling in groups. However, as a result of the machining technique chosen, a number of straight head-side surface(s) are created which run back as chords which are offset to the respective wheel circle formed by the respective cutting edge(s). This means that, although screw-in type artificial hip joint sockets with this kind of thread are relatively easy to screw in, they only have a reduced contact area to transfer forces because of the shortened thread tooth height. A special disadvantage is the formation of gaps in the area of the thread tooth head (individual thread teeth), between the implant and the bone, as well as the leverage forces acting on the bone substrate because of the excessively deep cut of the tooth flutes. This is the reason why screw-in type artificial hip joint sockets of this type are also deemed medically deficient.

Screw-in type artificial hip joint sockets of the type described above with a flat thread have only been able to claim a small fraction of the market to date. At the present time, screw-in type artificial hip joint sockets with so-called pointed threads are more wide-spread. However, these products are burdened in principle by the previously described complex problem with respect to unacceptable screw-in characteristics and the formation of a gap in the contact zone. The various attempts made to reduce the screw-in forces have actually, amongst others, resulted in an excessive widening of the milled tapping groove(s) to the detriment of the thread teeth. This means that valuable contact area is lost in conjunction with the formation of extended cavities and also reduced osary areas to absorb the forces.

In U.S. Pat. No. 4,997,447 a screw-in type artificial hip joint socket with round thread flutes is proposed in which the head surfaces of individual thread teeth run in a curve, whereby a relief angle is realized which reduces as the radius of this curve, seen from the socket pole, reduces with increasing distance from the cutting edge(s). In this screw-in type artificial hip joint socket, the degree of gap formation relative to the straight head surfaces is noticeably reduced without any loss of good screwing properties. However, this configuration does also not result in a full bone contact of individual thread teeth in the respective rear zones. Furthermore the manufacture of this product is extremely time-intensive, because the proposed design requires the complete traversal of the tooth head length with a milling machine.

Up to now, no products are available commercially in which screw-in type artificial hip joint sockets with pointed threads have individual thread segments with a relief angle. This is thought to be in connection with the fact that the implementation of such a design is extremely difficult and the initial choice of adopting milling techniques for production would require not only extremely complex programming but also very extensive machining times. These problems are due to the problem that in the case of pointed threads and depending upon the pattern of the tapping groove(s) at least one of the lateral surfaces of the thread tooth must be used to form a cutting edge(s). If, however, a neutral or relief angle is to be formed behind the cutting edge(s) then the corresponding lateral surface of the respective thread tooth must be back-milled to the subsequent tapping groove(s) at a congruent lateral angle. This creates the problem that the milling machine cannot machine curved surface shells while simultaneously following the contour of the base of the thread flute. One has then the choice of either accepting an increasing groove-like depression along the flank of the tooth or a correspondingly large stepped residual relict. In cases where this relict is unacceptable, it would then have to be removed subsequently using at least one additional milling run.

With the method according to the invention it is, however, possible to cut such threads for hip joint sockets with great perfection in a short time using lathing techniques. In so doing it is irrelevant whether the discontinuity machining to create a certain pattern e.g. a relief or neutral angle of individual thread teeth is to take place on its pole, its equator or its head side surface or on several of the surfaces. Because of the free programmability of the machining track it is not only possible to master any desired profile of the thread tooth but even the angular pattern of the generated thread rib sections are virtually freely selectable in three-dimensional space. At the same time the entire thread can be perfectly adapted to the outer shell of the socket body. Thus the invention can be applied to all known shell forms, e.g. spherical, aspherical, parapherical, conical-spherical, conical, cylindrical, parabolic, toroidal, etc.

The method according to the invention can be simply combined with other well-known methods for the production of threads for hip joint sockets, e.g. with the method as described in European patent EP 0 480 551 (CA 2,052,978) or with the method proposed in German publication DE 44 00 001 (U.S. Pat. No. 5,997,578) for the production of a thread with modifiable thread profile. A particularly beneficial combination appears to be a thread tooth profile inclined towards the socket pole and a thread pitch which changes smoothly according to international patent application WO 97/39702 (U.S. Pat. No. 6,146,425).

It is suggested in this regard in the invention that for artificial hip joint sockets with a tooth profile which tapers towards the head of the thread tooth, that the thread teeth formed between the tapping groove(s) are produced as so-called screw surfaces (sometimes referred to as screwed surfaces) and to selectively swivel them in their respective direction of extension depending upon the windup of the tapping groove(s). In this case screw surfaces are understood to mean those surfaces which are created by the rotation of a certain tooth profile with constant radial distance from the axis of the socket and with a pitch around this axis. In the case of for example trapezoidal tooth profiles this would mean three screw surfaces are formed, one on the head side and two on the lateral sides. In so doing, these screw surfaces may become shortened in their base area along their extension as the tooth profile sinks into the surface shell for certain shell geometries of the screw socket. The surfaces which follow the cutter at the start of the respective thread tooth will then have a neutral angle, i.e. neither a pinch nor a relief angle. This then avoids the undesirable pinching effects while at the same time ensuring bone contact on all sides of the thread tooth. In order to enable the cutting edge(s) to have the optimum effect at the start of each respective thread tooth, it must protrude in comparison to the leading thread tooth (preceding tooth in direction of screw rotation). In the first step this is achieved in that a larger radius is selected for the screw surfaces of a following thread tooth than for the screw surfaces of the leading thread tooth. Preferably, individual thread teeth are swung relative to one another in their extension as a function of the windup of the tapping groove(s), whereby the preferred direction of swing is one which approaches the windup angle in order to realize an overstand of the lateral cutting edge(s) with a positive cutting angle.

Another practical implementation of the invention in the production of these types of threads is to generate overshooting transition functions of the cutting track in specific positions on the thread length by programming hobble-jump(s) and to synchronize these with some form of interruption, e.g. in the form of tapping groove(s) such that during milling of the discontinuity the interfering or unusable parts of the contour generated are removed and that the cutting edge(s) following the discontinuity in the screw-in direction protrudes compared with the preceding tooth profile. The remaining part of the tooth blade then drops back compared with the cutting edge(s) such that behind the cutting edge(s) an area corresponding with a clearance angle (relief angle) is formed.

A further application of the invention concerns so-called circular wedges (or 3K couplings) in general mechanical engineering. These comprise a friction contact expanding coupling, for example between shaft and hub, which is a self-locking but releasable connection.

In the case of a circular wedge coupling, and in contrast to cylindrical cross-pressure locks, the joint connecting areas of the shaft and the hub are not round but have so-called wedge surfaces on the circumference. Generally there are three wedge surfaces. They comprise identical and reciprocally opposed turned sections of spirals, e.g. logarithmic spirals. When clamping by turning through a certain relatively small angular amount (e.g. 15.degree.) the necessary homogenous contact surface is achieved, and hence the maximum possible frictional connection between the shaft and the hub. Circular wedge coupling also provides for an excellent transfer of the respective forces and boast an advantageous rigidity of configuration. A coupling with three circular wedges on the circumference is self-centering. If the radial pitch of the wedges surfaces is selected between 1:50 and 1:200, circular wedge couplings are generally also self-locking.

If produced in sufficiently large numbers, and if the technical requirements are not too demanding, circular wedge profiles can be produced without cutting and hence relatively inexpensively. On the other hand, relatively smaller numbers, and to fulfill higher quality demands, has to date required either milling or grinding techniques with correspondingly high costs. The diameter of the milling tool or of the grinding disk results in the creation of transitions to the individual circular wedge areas which are unusable. In conjunction with the angle of twist required relative to the joints this means the coupling can only transfer a fraction of the potential forces.

Using the method according to the invention circular wedge couplings of this type can be manufactured using interleaved machining sequences with greater precision and at lower costs, even in small production numbers. The option is also created of machining couplings of this kind with a conical design if required.

BRIEF DESCRIPTION OF THE DRAWINGS

The invention is described in more detail with respect to the preferred applications based on twenty four schematic drawings. These are as follows.

DETAILED DESCRIPTION OF THE INVENTION

Figure 1:
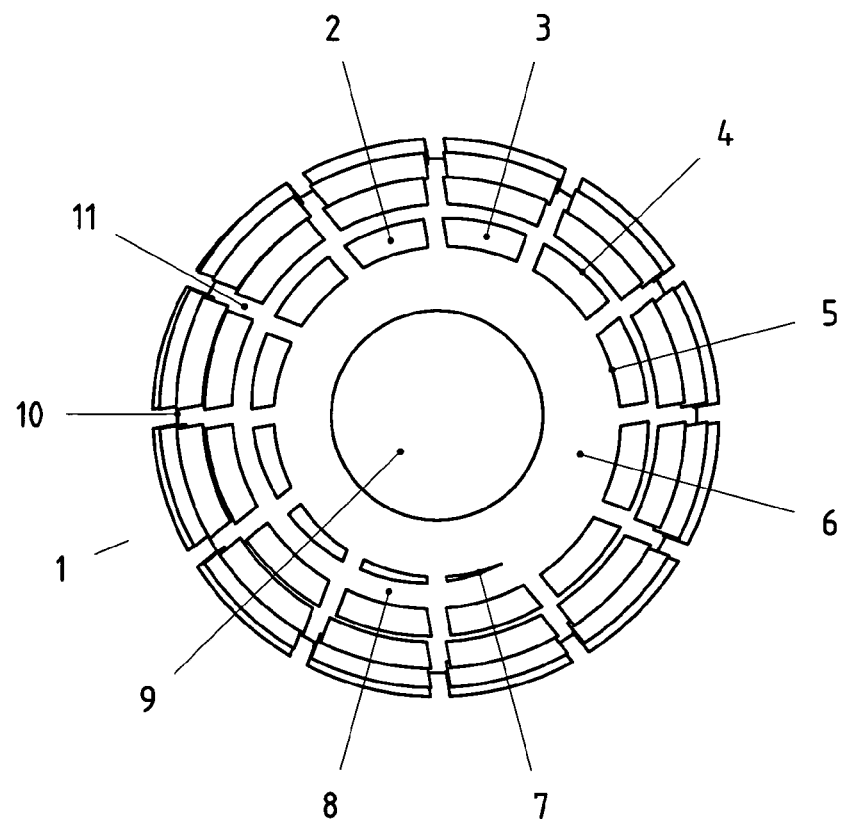
FIG. 1 Hemispherical screw-in type artificial hip joint socket with flat thread jamming on the head side according to state-of-art technology FIG. 2 Hemispherical screw-in type artificial hip joint socket with a flat thread having a clearance angle according to state-of-art technology FIG. 3 Hemispherical screw-in type artificial hip joint socket machined according to the invention with a flat thread made up of thread teeth with head-side screw surfaces FIG. 4 Hemispherical screw-in type artificial hip joint socket according to the invention with a pointed thread made up of thread teeth with screw surfaces on all sides FIG. 5 Two thread teeth of the screw-in type artificial hip joint socket according to FIG. 1

The drawing in FIG. 1 presents the pole-side view of a hemispherical screw-in type artificial hip joint socket 1 with a flat thread according to state-of-the-art based on an example with a 1.3 magnification. In the example the nominal diameter is 54 mm, the average tooth height is 2.6 mm, the pitch is 5 mm and the bottom hole diameter is 22 mm. These basic dimensions were selected for technical drawing reasons and are also retained in drawing FIGS. 2 through 4 to allow better comparability. Similarly, the windup angle of the tapping groove(s) has been set at 0.degree. throughout in order to reduce the drawing work. It is known that a woundup tapping groove(s) offers advantages with respect to a more favorable cutting angle and a more evenly distributed transfer of forces.

A dome shaped thread-free area 6 on the shell body continues from the bottom hole 9 of the screw-in type artificial hip joint socket 1. In the drawing the diameter of the shell body is represented by the equatorial margin area 10. The thread starts on the pole side at first thread tooth 7 and reaches its full height before thread tooth 2. Two of the thread teeth 2, 3 are marked with identifying numbers and are further detailed in detail drawing FIG. 5. Both the head-side surface(s) 4 and the edges 5 formed at the base of the tooth at the shell body of individual thread teeth—with the exception of the starting and end zone of the thread length—appear to be on a spiral-shaped curve in the two-dimensional drawing. The overall thread length has approximately 4 circuits. The thread groove bottom 8 running between the thread teeth forms the hemispherical shell of the shell body. In order to create tapping groove(s) 11 or cutting edge(s), the circumferential thread rib is slotted twelve times without wind-up. In so doing the slotting dips at an angle of around 10.degree. in order to form in each case a positive cutting angle at the individual thread teeth.

Figure 2:
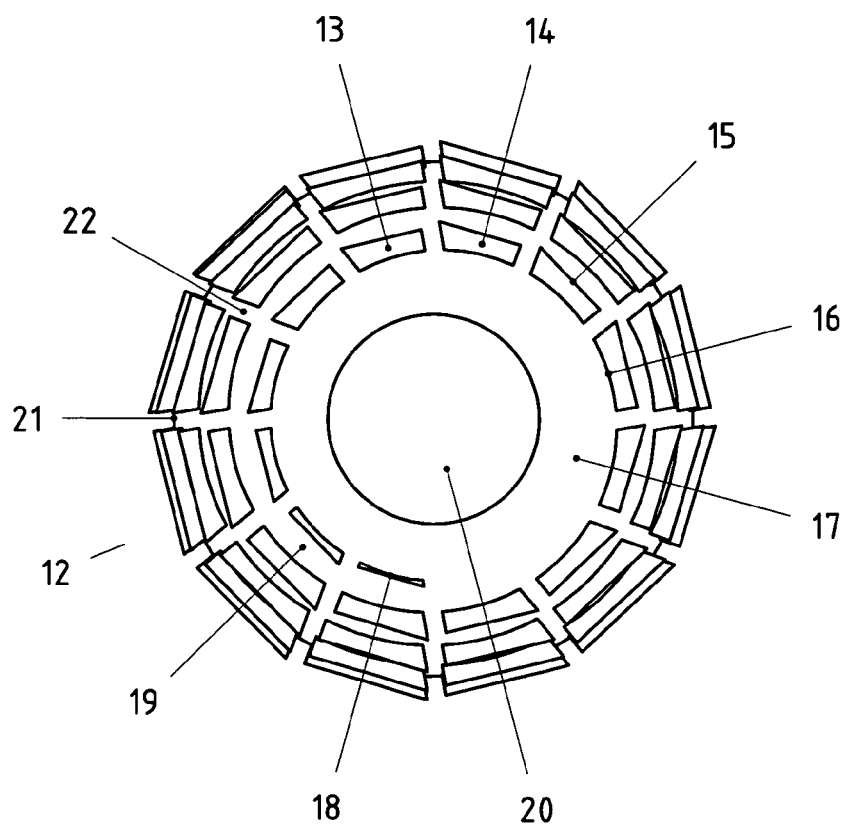

The example shown in FIG. 2 of a screw-in type artificial hip joint socket with a flat thread according to state-of-the-art is produced from screw-in type artificial hip joint socket 1 by after-milling. In the diagram the bottom hole 20, the dome area 17, the thread groove bottom 19, the nominal diameter 21, the slotting 22, the edges 16 between the thread teeth and the shell body all correspond completely with FIG. 1. In order to maintain a constant average threaded tooth height the thread teeth were individually milled because of the hemispherical shell body. In so doing the pole-side start of the thread moved to thread tooth 18. The straight outer surface(s) 15 of individual thread teeth now run as chords to the wheel circle of the leading head-side cutting edge(s) in the screw-in direction and in synchronization with the thread slotting. such that relief angles are formed with respect to the respective wheel circle. The effect of the cutting edge(s), of reducing the screw-in forces, is achieved by the circumstance that the radial distance of the cutting edge(s) from the socket axis is always larger than the corresponding radial distance of the leading edge of the blade. Two of the thread teeth marked 13 and 14 are detailed below in FIG. 6.

Figure 3:
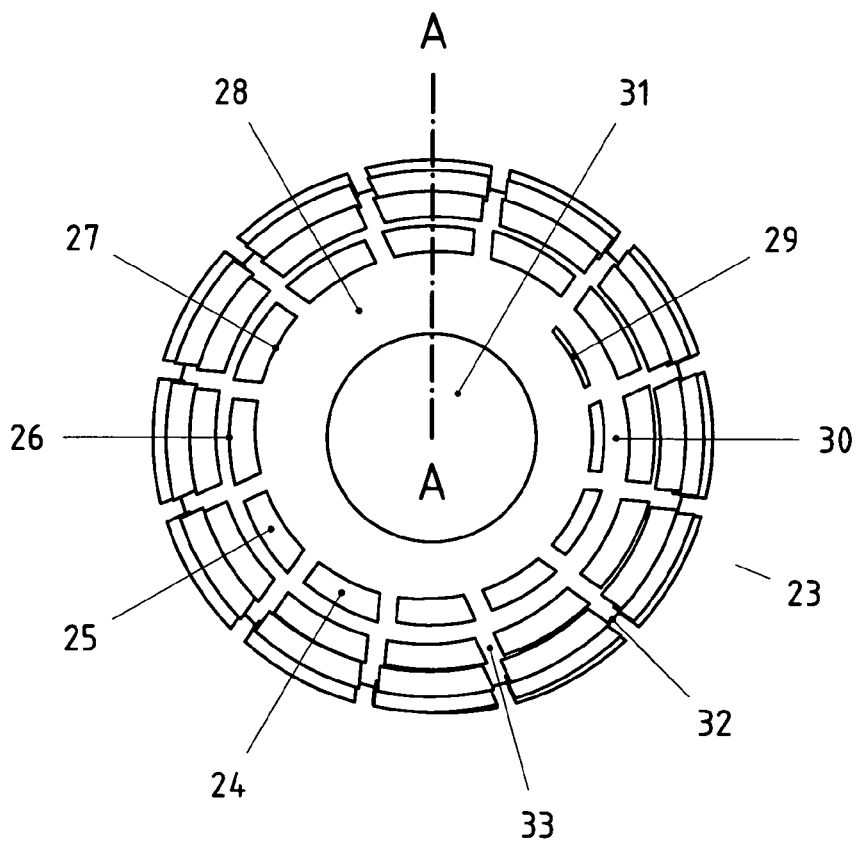

The example illustrated in FIG. 3 is a screw-in type artificial hip joint socket 23 machined according to the invention method and corresponds in its hemispherical shell, its basic dimensions, bottom hole 31, dome area 28, the edge 27 between the thread teeth and the shell, the base of the thread 30, the diameter 32 and the thread slotting 33 with the example in FIG. 1. The thread length of the flat thread starts with a reduced tooth height in the first thread tooth 29 which then increases in jump(s) in the next sequence of four thread teeth until the thread rib reaches its full height in thread tooth 24. The parallel flank(s) of each individual thread tooth border in each case on the outerlying section of a cylindrical surface 26 which is coaxial to the screw-in type artificial hip joint socket axis, whereby the basic cylinder diameter increases in steps from thread tooth to thread tooth. This design principle can also be achieved with a respective section from a correspondingly coaxial screw surface. This design as described forms neither a pinch nor a relief angle at the thread teeth. Indeed a relief angle is absolutely not necessary because the surface roughness (e.g. caused by sand blasting of the screw-in type artificial hip joint socket surface) creates filing forces which, assuming a neutral relative movement, prevent any sticking during the screw-in method. This means the undesirable formation of a gap between the implant and the bone layer is avoided. Despite this, the front outerlying cutting edge(s) of the thread tooth is effective because it has a larger radial distance from the socket axis than the leading cutting edge(s). This results in slightly lower screw-in forces with average tactiliance and improved primary and secondary fixation of the implant.

Figure 4:
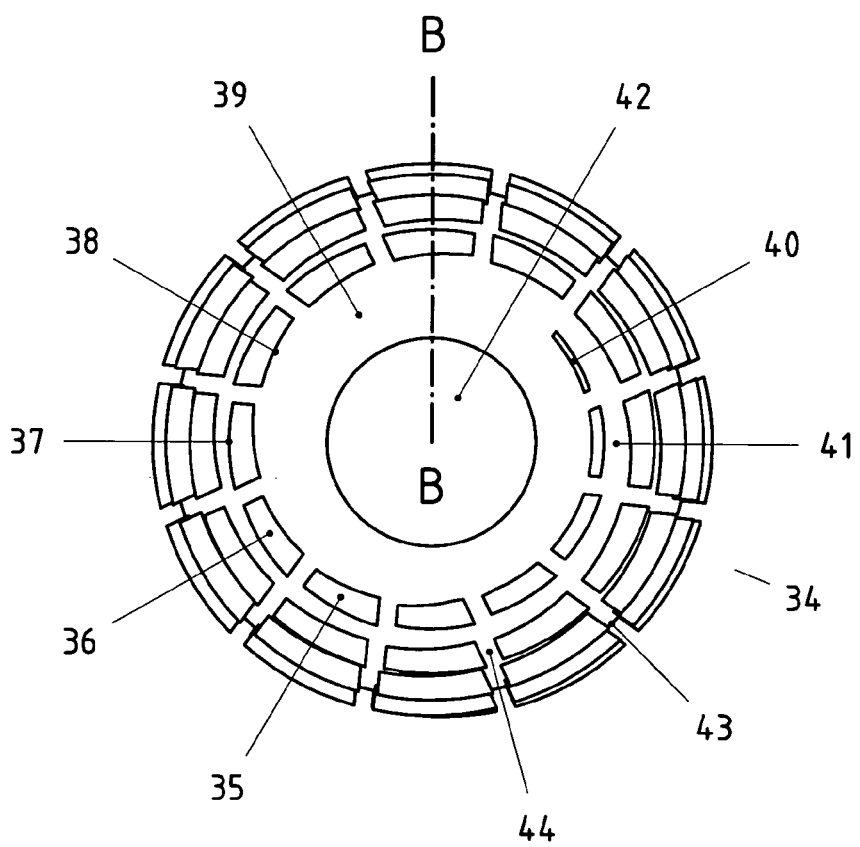

The example of a hemispherical screw-in type artificial hip joint socket 34 machined according to the method according to the invention is illustrated in FIG. 4. Here again the various individual details, i.e. the bottom hole 42, the dome area 39, the base of the thread 41, the diameter 43 and the thread slotting 44 are the same and unchanged from the previously described examples. In contrast to these, however, the thread described is a pointed thread comprising in principle a triangular thread tooth profile. This fact is not apparent from the two-dimensional drawing. In a similar fashion to the above, the thread length commences with an initial small thread tooth 40 and the tooth height increases step-wise over several stages and reaches its final (average) tooth height at thread tooth 35. The edge 37 formed at the tooth head (individual thread tooth), which in the case of a pointed triangular cross section of the threaded tooth is practically only a line, comprises for each individual thread tooth a screw line with constant distance from the axis of the screw-in type artificial hip joint socket which is shown in the diagram only as an curve with a fixed radius to the socket center. In the case of the pointed thread chosen, the lack of windup of the tapping groove(s) 44 means a cutting edge(s) is formed at both thread tooth flank(s). The cutting edge(s) would shift to one of the threaded tooth flank(s) if the tapping groove(s) had there been a corresponding wind-up (tapping groove slant). The surfaces on both sides of any individual thread tooth of the example shown comprise screw surfaces whereby the pitch of the pole-side surface corresponds with the pitch of the equator-side surface even if the optical impression seems to indicate otherwise because of the socket diameter which increases towards the equator. Because of this, the edge 38 formed at the base of the tooth between the thread tooth and the shell of the screw-in type artificial hip joint socket appears to run backwards into the shell. After adopting a larger radial distance from the socket axis for the screw surfaces of the next subsequent thread tooth during screwing in, the cutting edge(s) on both sides can be either lateral to the thread profile of the leading thread tooth or protrude radially outwards and will, as such, cut easily during screwing-in. In this case again, the neutral angle created by the extension of the thread tooth means that the creation of gaps in the contact area to the bone is avoided.

The statements made in the preceding regarding state-of-the-art and the examples of the method according to the invention are explained in greater detail in the magnified details presented in the following figures because certain details are only difficult to recognize in the overall diagrams.

Figure 5:
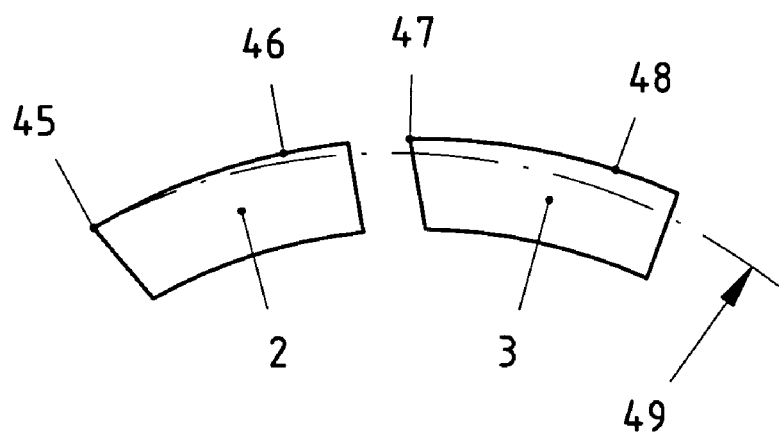

In FIG. 5, two thread teeth 2, 3 are enlarged from FIG. 1. Of these, thread tooth 2 has a cutting edge 45 located on the front of its head-side surface 46 and thread tooth 3 has a identical cutting edge 47 on the corresponding surface 48. The wheel circle 49 which has a fixed radius around the central axis of the socket and which is described by cutting edge(s) 45 during screwing in of the screw-in type artificial hip joint socket is marked in as a dot—dash line. It is easy to see that part of the respective thread teeth extends beyond the wheel circle, which in general will lead to blocking effects.

Figure 6:
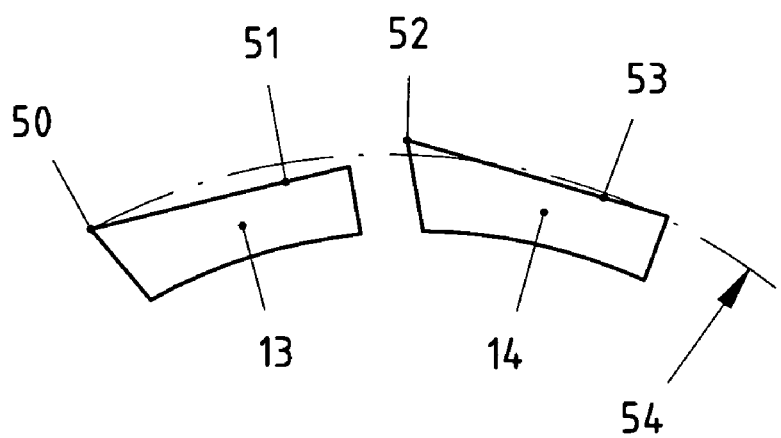
FIG. 6 Two thread teeth of the screw-in type artificial hip joint socket according to FIG. 2

FIG. 6 shows details of thread teeth 13, 14 according to the example illustrated in FIG. 2 and will not result in blocking effects because the surfaces 51 and 53 on the head side following cutting edges 50 and 52 are milled with a relief angle. In so doing the dash-dotted wheel circle 54 of cutting edge 50 does not touch the head-side surface of the thread tooth at any point. It is, however, true that each of these cases creates undesirable free play. This free play is larger, the smaller the number of tapping groove(s). This means that in particular screw-in type artificial hip joint sockets with for example only six tapping grooves will be extremely disadvantaged. The design shown is frequently used for conical screw-in type artificial hip joint sockets because then the thread teeth can be very rationally milled in so-called packages. Medically speaking, however, this argument bears no weight and should be rejected.

Figure 7:
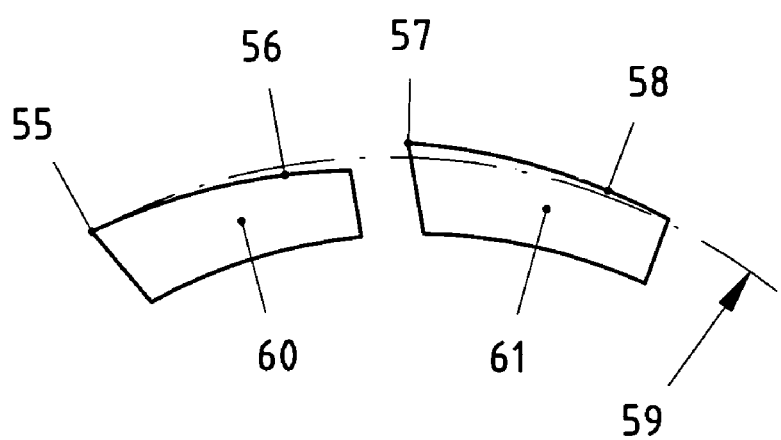
FIG. 7 Two thread teeth with clearance angles and arc-shaped head surfaces

The problem described above can be ameliorated to a certain extent by adopting a design of the thread teeth 60, 61 according to FIG. 7. Here again the head-side surface(s) 56, 58 of the thread teeth (i.e., apex, crown, ridge) have a relief angle with respect to the wheel circle 59 behind the leading cutting edge(s) 55 and 57. This effectively prevents jamming during screwing in. However, because of the curved shape of surfaces 56, 58, the gap-forming free play is relatively small and is therefore more acceptable. On the other hand, however, this arch shape is concomitant with a much greater milling complexity and effort because individual thread teeth have in principle to be tangentially traversed individually during manufacture. In the method according to the invention the geometrical configuration illustrated of individual thread teeth can be produced much more rationally in only a single clamping on a CNC lathe.

Figure 8:
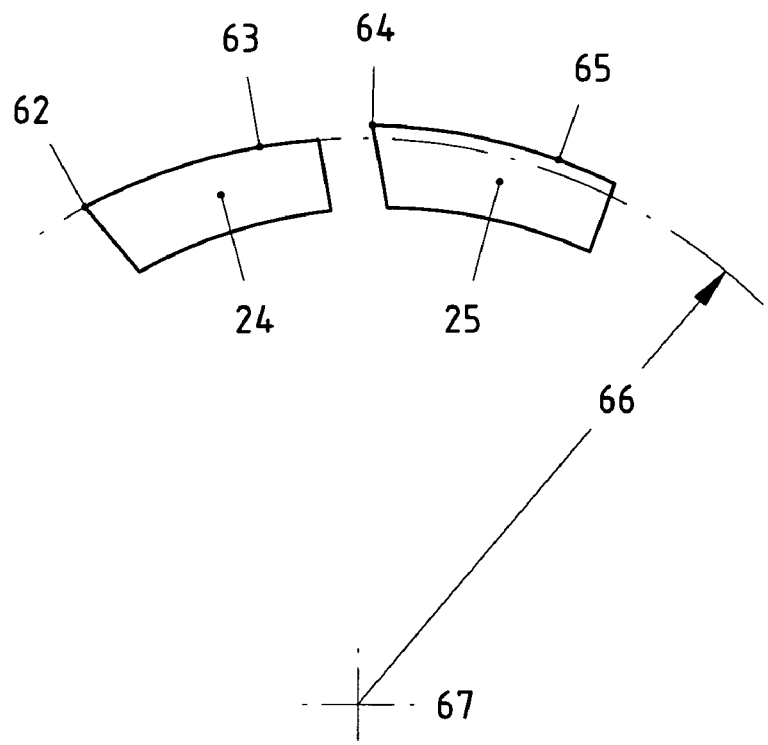
FIG. 8 Two thread teeth of the screw-in type artificial hip joint socket according to FIG. 3

In comparison, the configuration of the respective outer surfaces of individual thread teeth—as so-called screw surfaces—using the method according to the invention, and as described previously in FIG. 3, is shown in FIG. 8 in the form enlarged depictions of two thread teeth 24, 25. The head surfaces 63, 65 of the thread teeth extending from cutting edges 62 and 64 respectively have a fixed radius which is defined in each case as the distance of the cutting edges from the screw-in socket axis 67. Therefore the wheel circle described by cutting edge 62 and depicted in the drawing as a dash-pointed line with fixed radius 66 is coincident with the head surface 63. Since the corresponding radius of thread tooth 25 is larger, its cutting edge 64 extends or projects beyond the leading cutting edge 62 of thread tooth 24 during screwing in. This means that the respective cutting edge(s) and the subsequent front area, set at a positive cutting angle, both penetrate/cut into the bone material and can transport the cuttings away in the tapping groove(s) with a relatively light cutting force.

Figure 9:
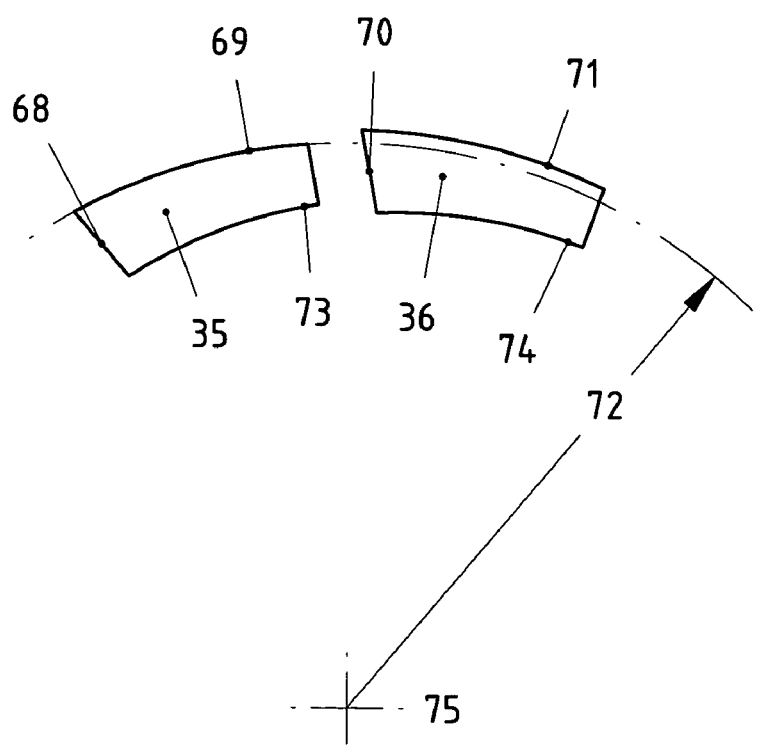
FIG. 9 Two thread teeth of the screw-in type artificial hip joint socket according to FIG. 4

The situation in FIG. 9, showing an enlargement of a section of FIG. 4 differs from that described in FIG. 8 in that the thread does not have a flat thread in its tooth profile but a pointed thread. Here again, however, the outer surfaces of individual thread teeth 35, 36 are each designed as screw surfaces. Because of the inclined lateral angle and the pitch or the angle of the thread teeth, and the hemispherical shell contour, the edge formed at the base of the tooth to the shell jacket appears to run into the edge at its rearward end 73, 74. In fact, however, when the screw-in type artificial hip joint socket is rotated there is no radial shift of the projected tooth cross section because the respective outer edges 69, 71 are unchanged in their radius to the screw-in type artificial hip joint socket axis. By bringing in a triangular tooth cross section for the example shown, there is a shift of the respective cutting edge of at least one lateral surface of the respective thread teeth, and in the case of tapping grooves without wind-up, on both lateral surfaces. The drawing shows only the pole-side cutting edge 68, 70. The respective rearward cutting edge is hidden. The wheel circle of the head-side threaded tooth edge 69 is shown with fixed radius 72 around the screw-in type artificial hip joint socket axis 75. The extremely reduced screw-in forces of this design are the result of the mutual radial offset of individual thread teeth as a result of which the individual cutting edges stand out both laterally and outwardly compared with the respective leading cutting edges.

Figure 10:
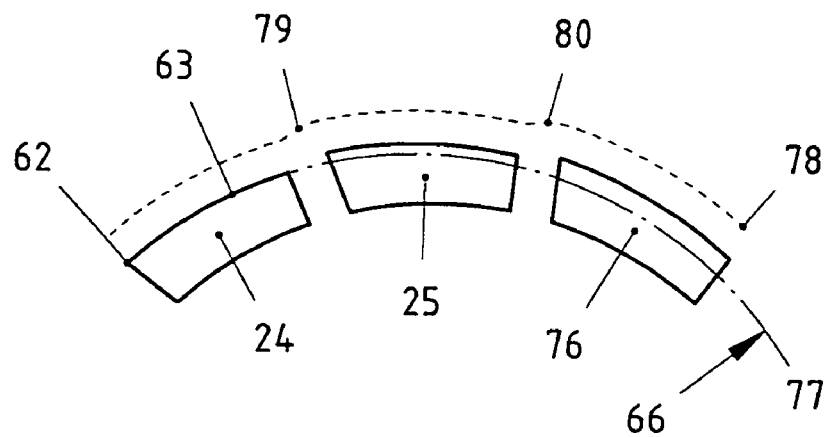
FIG. 10 Three thread teeth of the screw-in type artificial hip joint socket according to FIG. 3 and high-dynamic tool track FIG. 11 Three thread teeth of the screw-in type artificial hip joint socket according to FIG. 3 with a tool track of average dynamics using the hobble method FIG. 12 Three thread teeth of the screw-in type artificial hip joint socket according to FIG. 3 and over-swinging tool track with the hobble method FIG. 13 Theoretical tool track generated with jump commands FIG. 14 Workpiece contour generated from transition functions FIG. 15 Final workpiece geometry after further processing FIG. 16 Sleeve for a circular wedge coupling FIG. 17 Journal for a circular wedge coupling FIG. 18 Half-side sectional view of the screw-in type artificial hip joint socket according to FIG. 3
Figure 11:
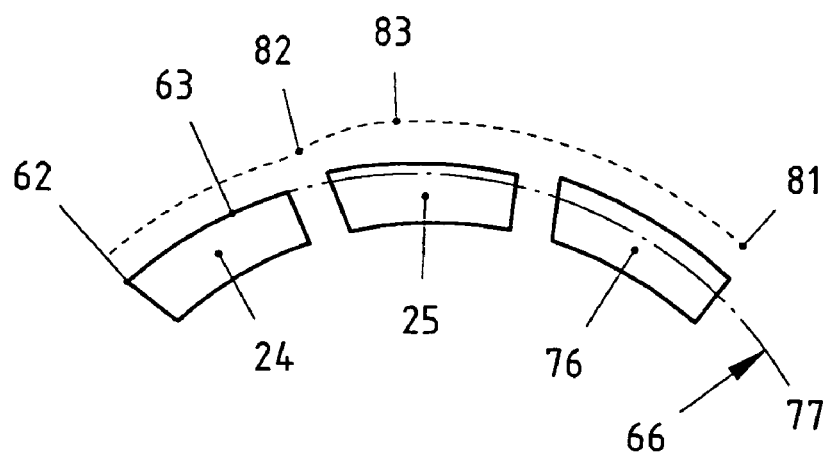
Figure 12:
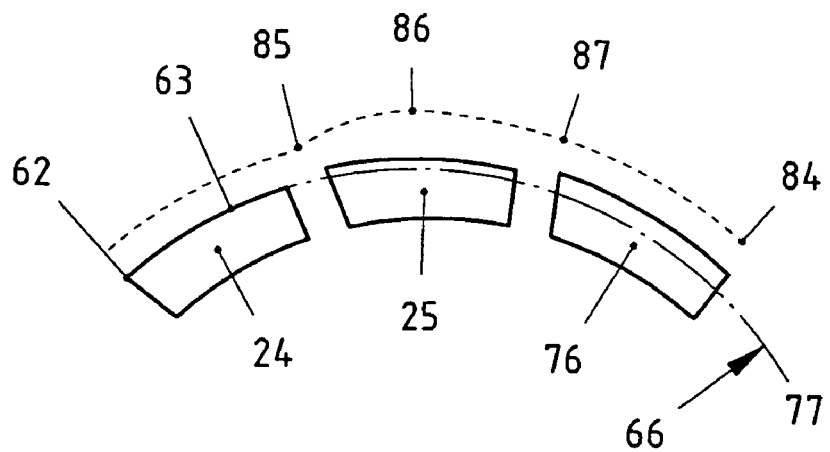

In order to understand the procedure to implement the method for the proposed preferred application for the production of a screw-in type artificial hip joint socket thread the features presented in FIGS. 3 and 8 are again referred to in FIGS. 10 through 12. In each of the Figs. the three thread teeth 24, 25, 76 of the flat thread are depicted as is cutting edge 62 on the head-side surface 63 with its dash-dot wheel circle 77, with the radius 66 around the screw-in type artificial hip joint socket axis. The scale of the figures is slightly reduced compared with the preceding figures.

FIG. 10 illustrates the track 78 of a machine tool (e.g. indexing cutter) which is equidistant to the head-side surface of the edge formed by the tooth head, whereby the track is achievable in the configuration shown using a program according to the invention comprising a small number of target points (locations) with an extremely dynamic lathe or a correspondingly dynamically driven tool. The distance of the track from the contour to be cut was selected in order to make the course of the track visible over its entire length. Track 78 contains two discontinuities 79 and 80 which are deliberately placed in those positions by the programming in order to allow subsequent machining of the slotting of the thread using milling techniques. Although the discontinuities 79, 80 of track 78 are transitory in function, it has the effect of creating a radial jump function between sequential thread teeth. This radial jump function exists in every case with respect to the proposed programming whereby at least two sequential following co-ordinates of the same diameter have to be entered with a traverse in Z adapted to the machining task and a suitable pitch or suitable spindle angle and followed by a diameter jump at maximum advance speed (e.g. 100 mm/rev). In order to achieve an acceptable machining result it is necessary that the transition area on the workpiece is not wider than the intended width of the tapping groove(s).

The creation of the cutting track as shown in FIG. 10 is not even possible using a linear drive tool because the overall dynamics of the system are insufficient in order to move any compound seat with the necessary precision within the required path on a different lathing diameter. With the invention the proposal in this case is a jump method with which this problem can be overcome in principle. The corresponding theoretical background is clarified in FIG. 11. The machining procedure for track curve 81 suggests only machining for example the 1st, 3rd, 5th, 7th etc. thread teeth in a first machining cycle and skipping the 2nd, 4th, 6th etc. In this case the transitional function of track 81 arising from the programming of the jump function and in connection with the machine damping need only be sufficient such that after location 82 the reaction is, for the tool to be lifted over the next following cutting edge, merely enough not to round it off or damage it. There is room up to location 83 to return the tool to the desired track, and this is not limited by the width of the tapping groove(s). It is then possible without difficulty in a second machining cycle to complete the contour elements skipped and to similarly skip those machined previously.

In the case of older lathes with corresponding inertia in control circuits it must be taken into account that an over-response will result in a distortion of the track curve. This effect is shown clearly in track 84 in FIG. 12. Following the abrupt reaction of the tool movement to the programmed task at location 85 there is an over-oscillation of the track which reaches its maximum at location 86. This is then followed by a soft build down transition until the track is again on the programmed course at approximately location 87. In this example the described effect would still be just about controllable using the suggested jump method in two machining cycles. If necessary the jump method could, however, be extended to comprise of three or more cycles.

The variations as above describe a method which is equally applicable to inclined tooth head surfaces as well as to the lateral surfaces of thread teeth, for example as per FIG. 9. In this the described jump function is shifted either completely or partially from the X-axis to the Z-axis. In these cases the hobble tracks described by the tool have not been illustrated in the drawing, but do correspond in principle to those jump methods shown for the machining of tooth heads (individual thread teeth)s.

Figure 13:
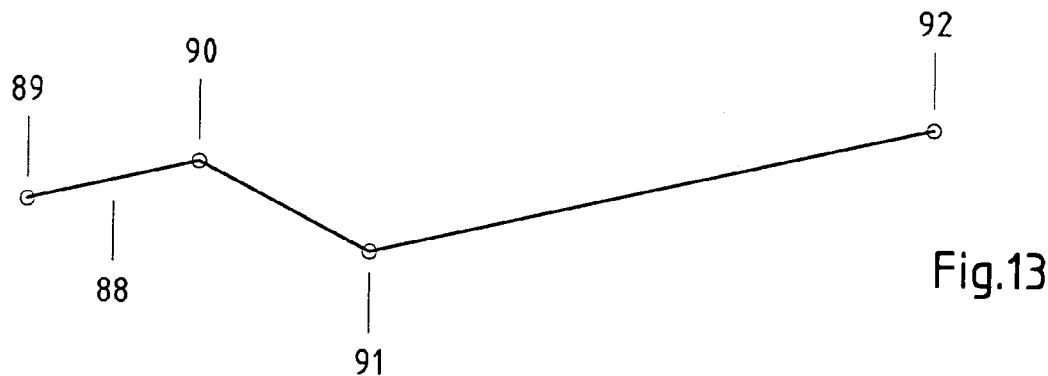
Figure 14:
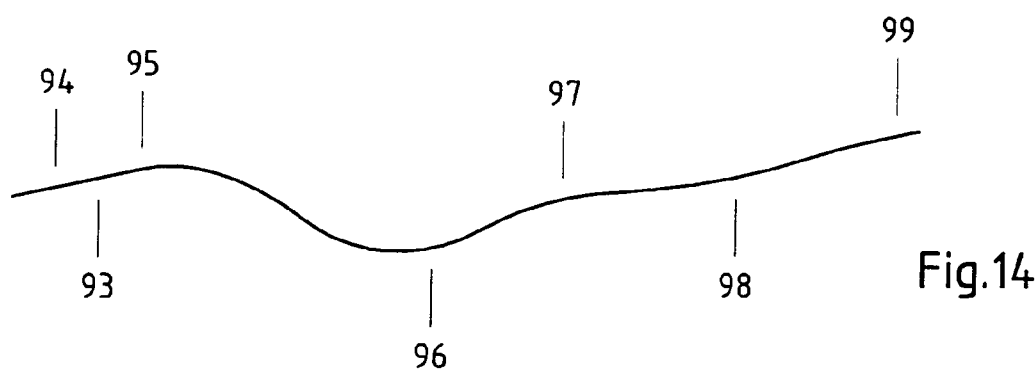
Figure 15:
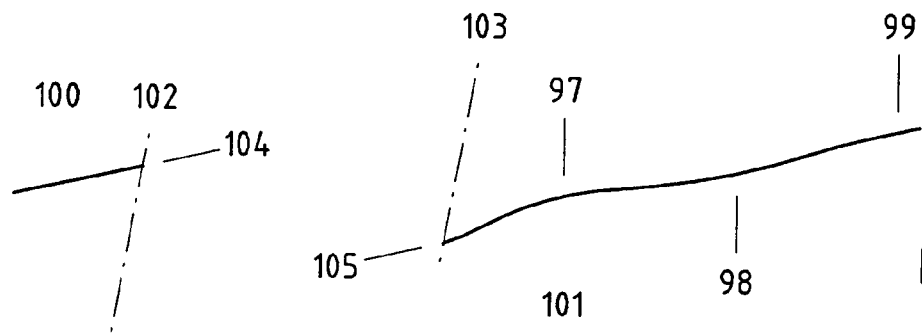

As described previously the invention also opens up the possibility of directly exploiting the overshoot behavior of the machine for the creation of relief angles on thread teeth. The exact procedure is described in more detail in FIGS. 13 through 15. FIGS. 13 through 15 show three curves on an enlarged scale based on the example of staggered tooth flank which have been reduced to the interesting movement section of the tool track for transparency by leaving out the spatial components. In practice this movement could be on one or more levels.

FIG. 13 shows the tool track 88 commanded in the program using a single jump command. Coordinate locations 89, 90, 91 and 92 are specified using corresponding values for X and Z. Of these only the modification of Z is a shown on the drawing sheet as vertical components, whereas the respective value of X is not apparent in the drawing. The horizontal spacing between the coordinate locations is proportional to the respective spindle angle, which can be programmed either directly via parameter spindle angle C or indirectly via the pitch (F). In so doing it should be noted that if parameter F is also used the maximum permitted value of the pertinent NC control must not be exceeded, whereas in the case of the spindle angle programming of the angular jump, 0.degree. can be set without problems. In principle a number of jump commands can also be linked with one another.

FIG. 14 shows that the configuration of a threaded tooth flank measured on the workpiece before the milling of the tapping groove(s), as results from the command chain as per FIG. 13

The curve 93 in the figure comprises transitional functions which are based on the inertia and the standard rigidity of the machine and the control. The curve starts with a smooth course 94, and is abruptly redirected at location 95, in synchronization with the jump command. The location of maximum overshoot is location 96, which is followed by a return swing 97. After this there is a small amplitude afterswing 98 before the curve returns to a steady course 99.

FIG. 15 shows the lateral workpiece contour after the production of the tapping groove(s). The flanks of the tapping groove(s) are indicated by two dash-pointed lines 102, 103. These form the flanks 100, 101, of two thread teeth. The position of the tapping grooves is synchronized with the contour of the threaded tooth flank in such a way that on the one hand the end 104 of the leading thread tooth is located in front of jump location 95, and on the other hand that an overstand with a relief angle is formed on cutting edge 105 at the following thread tooth. The small bump 98 formed by the afterswing has an amplitude which is dependent both on the mass and the control inertia of the system, as well as for example on the cutting speed used. It is, however, of practically no significance for the general effectiveness of the primarily generated protruding cutting edge(s) and the relief angle.

The curve shown as an example in the drawing of two sequential threaded tooth flanks also includes a mutual swing of individual thread teeth in their direction of propagation. The amount of this swing depends on the design specifications. The swing can be either minimized or completely eradicated such that only a relict of the overshoot (96) remains in the form of cutting edge 105, or a part thereof, which extends beyond the end 104 of the leading thread tooth.

The method explained with the help of drawings 13 through 15 can be applied in a corresponding fashion in for example flat threads on radial tooth heads (individual thread teeth) pointing outwards as well as on other threads on two or more surfaces of the threaded tooth profile.

Figure 16:
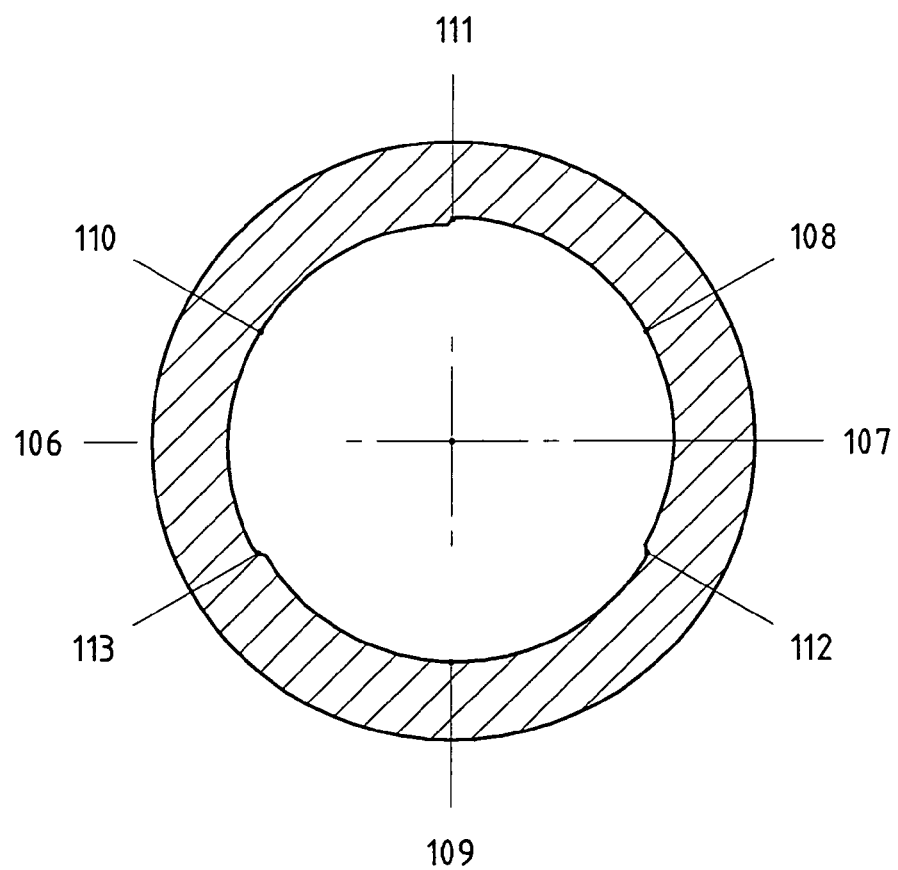
Figure 17:
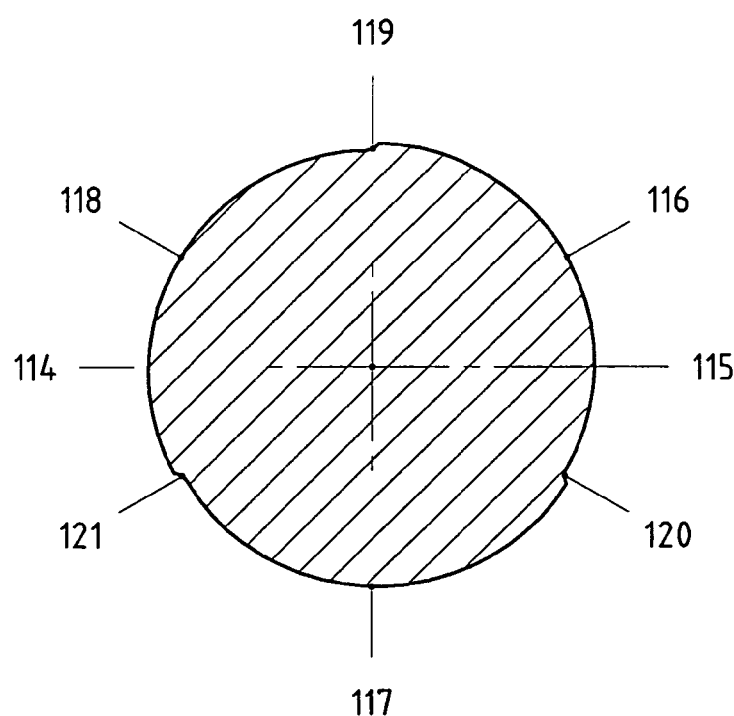

A further application of the method according to the invention is presented in FIGS. 16 and 17 based on an example. In this case this is a so-called circular wedge coupling which is used in general mechanical engineering. FIG. 16 shows a coupling sleeve 106 with a center 107. The inner wall has three circular wedge surface(s) 108, 109, 100, which abut on each other at jump(s) 111, 112 and 113. A journal 114 adapted to the inner profile of sleeve 106 is illustrated in FIG. 17. This journal has three outer circular wedge surface(s) 116, 117, 118 centred around the central axis 115 which cross over into one another at jump(s) 119, 120, 121. The circular wedge surface(s) present on both sleeve 106 and journal 114 are sections of spirals which end and begin abruptly at the respective abutment points. In order to produce these circular wedge surface(s) using the method according to the invention it is in principle irrelevant whether these are sections from an archimedial, a logarithmic, hyperbolic or Fermatic spiral. One would, however, generally assume that a circular wedge surface is a section from a logarithmic spiral because this generates the most favorable material loads during clamping because of the uniform angle of pitch.

When producing inner or outer circular wedge surfaces the significant aspect is that the curvature is mainly according to the specifications and that the jumps waste as little as possible of the future contact area. This task is achieved without any difficulties using the method according to the invention including the jump system described in the preceding. In order to cut for example the circular wedge sleeve 106 on a CNC lathe, a suitable blank is initially predrilled and if necessary rough machined to achieve initial dimensions. The final machining using a drill rod, for example with an index cutting tool is in principle such that during workpiece rotation the tool is moved radially outwards at a slow rate of advancement to the end of the circular wedge surface and then is lifted from the circular wedge surface by a jump command directed inwards. This jump command in the program creates a tool track comprising a transitional element with an overshoot pointing towards the center 107 which is dimensioned in the programming such that the tool is a considerable distance from the start of the next circular wedge surface. The following command blocks in the program are configured such that the next circular wedge surface is skipped and the tool is introduced to the next but one circular wedge surface when its track has settled. In the case of the example illustrated in FIG. 16, which requires a relative movement of the workpiece to the tool in a right-handed turn, looking in the direction of view, the machining sequence of the three circular wedge surface(s) 108, 109, 110 would then for example be as follows, starting with circular wedge area 108:

108—machine from 112 to 111
110—skip
109—machine from 113 to 112
108—skip
110—machine from 111 to 113
   109—skip
   108—machine from 112 to 111
   etc.

There are a number of freedoms with respect to the configuration of the NC program according to the invention. Thus for example the radial advance can be programmed as pitch, with the choice of using a superimposed modifying function, (e.g. using parameter E), or as fixed co-ordinates, in order to realize a specific form of surface curvature. As far as the axial tool movement is concerned there is the choice of either retaining the corresponding tool advance and hence using smaller advance values or only employing advance either during the cutting of the individual circular wedge surface(s) or the cutting pauses during skips.

The production of the journal required for the circular wedge surface(s) corresponds in principle the procedure described for the sleeve. An appropriate tolerance of the dimensions should be borne in mind such that both parts fit together with the requisite gap. The jump surfaces created by machining according to the invention only represent such a small part of the circumference that between the fitted partners only negligible gaps are not used for the transfer of forces.

In fact the possibilities opened up by this method are virtually unlimited. They are generated by the application of CNC programs by linking with the movement of a tool fixed to a carriage with the rotation of the spindle and the inclusion or the combination of hobble values for the address parameters for diameter, length and pitch or spindle angle as well as the possibility of using a reciprocal-step technique or the described interleaved machining sequences. Thus it is now possible to run machining tasks on CNC lathes extremely rationally which previously were very time consuming and in part had to be produced in poorer surface quality by milling.

The proposed artificial hip joint sockets with special threads and thread teeth of screw surfaces with neutral angles behind the cutting edges as proposed for the application of the method is desirable because of the very low screw-in forces, extremely low risk of overtightening, excellent tactiliance and a for the most part gap-free transition to the bone bearing surface. A particularly advantageous model is such with a pointed thread, tapping grooves with windup and thread teeth swung relative to one another in the direction of the wind-up angle. This not only makes handling of the screw socket considerably better during implantation but also substantially increases primary and secondary fixation and hence virtually excludes the risk of premature loosening.

Figure 18:
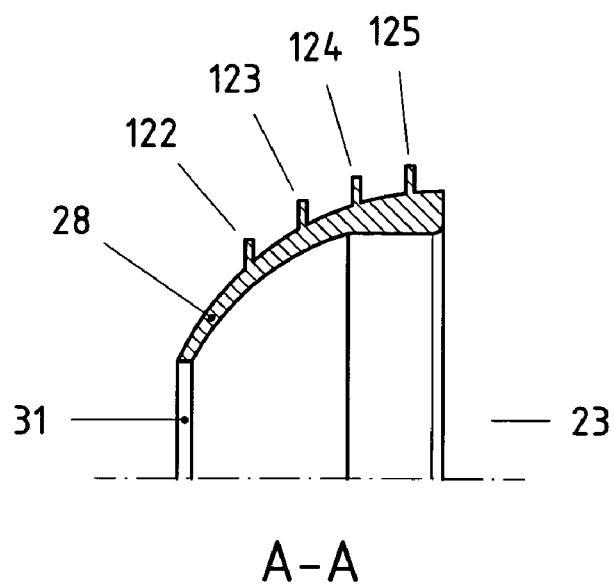

FIG. 18 is added for better understanding of FIG. 3. It shows a half side sectional view A-A of the screw-in type artificial hip joint socket 23 according to FIG. 3. The shell 28, having a bottom hole 31, is equipped with teeth 122, 123, 124 and 125. The teeth are realized in the typical shape of a flat thread.

Figure 19:
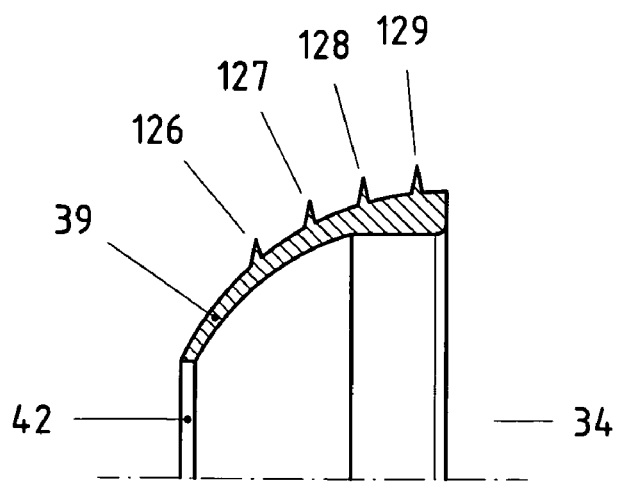
FIG. 19 Half-side sectional view of the screw-in type artificial hip joint socket according to FIG. 4

FIG. 19 shall serve for the same purpose as FIG. 18. It shows a half side sectional view B-B of the screw-in type artificial hip joint socket 34 according to FIG. 4. The shell, having a bottom hole 42 as before, is equipped with teeth 126, 127, 128 and 129, which now are realized as a pointed thread.

Figure 20:
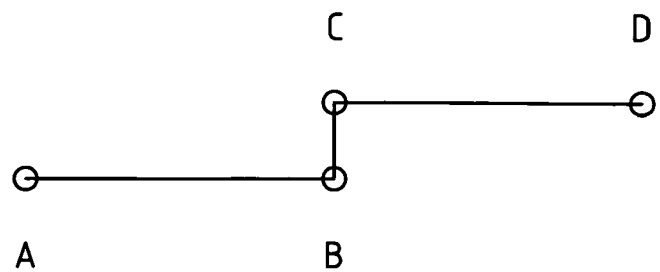
FIG. 20 Tool track program for a single jump function

FIG. 20 shows a turning lathe tool track program for a single jump function as a schematic diagram. The program starts with a position A, then moves to a second position B, jumps to a position C, and moves on to a destination D. The general pitch of the turning lathe tool movement in this example then is present as the procession A to D.

Figure 21:
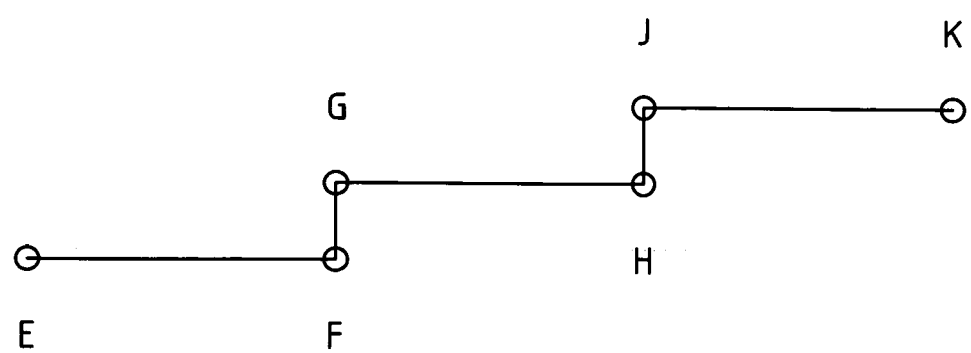
FIG. 21 Tool track program for a double jump function

FIG. 21 is used to show a simplified example of a double jump function in form of a coordinate chain described by points E, F, G, H, J and K. Jump functions are existing from F to G and from H to J. The true tool track movement (not shown) will consist of transition elements depending from the turning lathe turret response. The general pitch of the turning lathe tool movement then is present as the procession from E to K.

Figure 22:
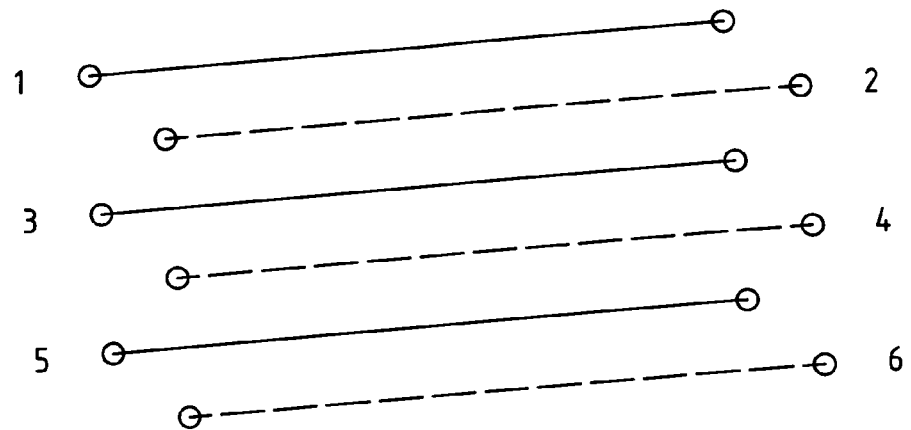
FIG. 22 Program for parallel tool tracks

A group of simplified, quasi unwound portions, of parallel turning tool paths are drawn out in FIG. 22. There is the choice of using two different tools, the first one being used for path 1, 3 and 5, shown as solid lines, the second one for path 2, 4 and 6, shown as dashed lines, or a single tool for a first set of paths 1, 3 and 5, and a second set of paths 2, 4 and 6. This kind of programming is state-of-the-art and not object of this patent application.

Figure 23:
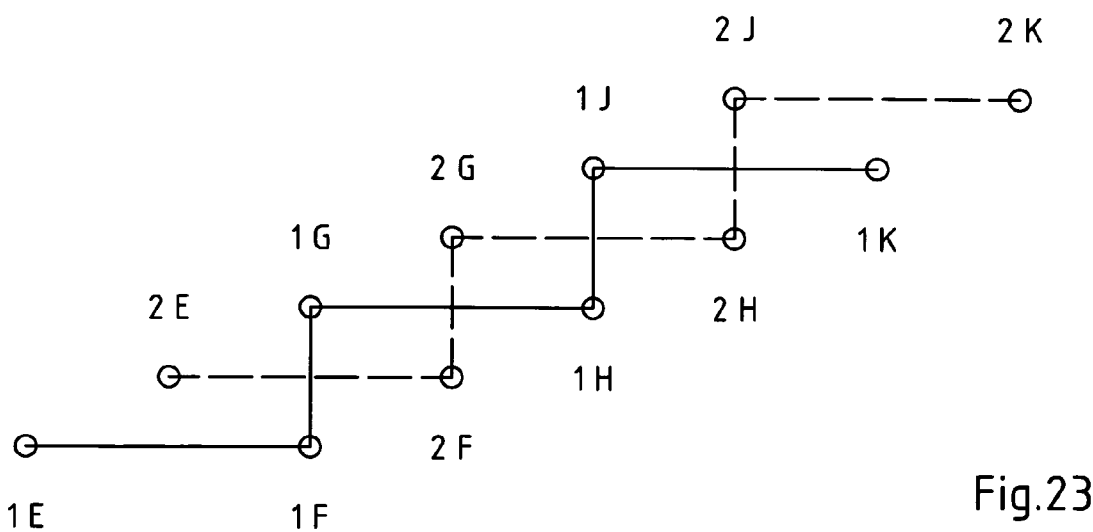
FIG. 23 Program for interlaced tool tracks with jump functions

Compared to FIG. 22 described before, FIG. 23 shows an interlacing kind of programming according to the invention. There are two coordinate chains, a first one by 1E, 1F, 1G, 1H, 1J, 1K, drawn out as a solid line, and a second one by 2E, 2F, 2G, 2H, 2J and 2K, drawn out as a dashed line. There is the choice of using two separate tools, one for the first and another one for the second coordinate chain, or to use the same tool for both tool paths. Within this example, the general pitch of the turning lathe tool track then is described as an interlaced procession from 1E to 2J or from 1F to 2K, where jump functions or jump steps are present from 1F to 1G and from 1H to 1J, respectively from 2F to 2G, and from 2H to 2J.

Figure 24:
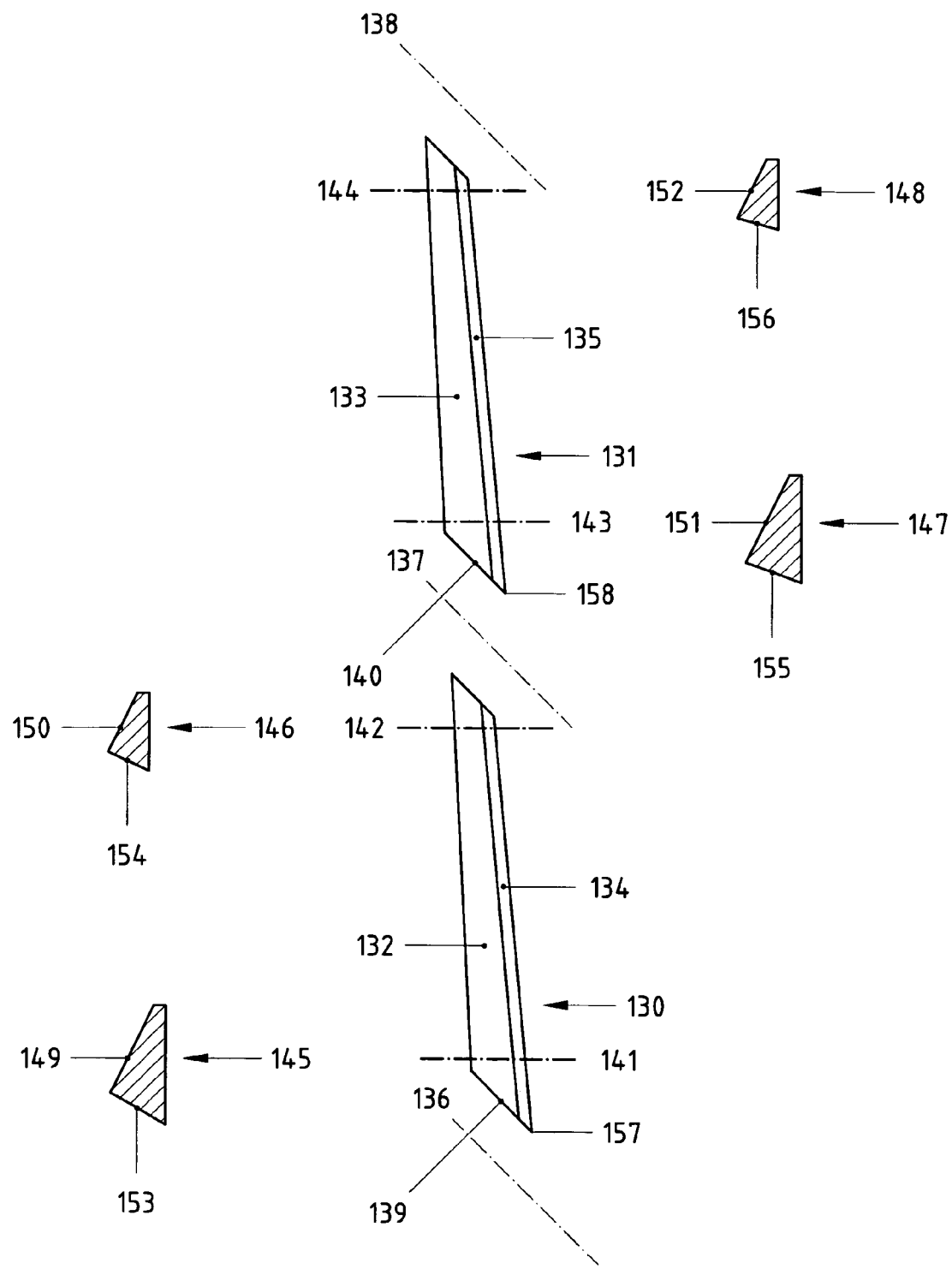
FIG. 24 Developed thread rip procession with thread blades having clearance angles

FIG. 24 shows two thread blades, also called thread wings or thread teeth 130 and 131, unwound from a threaded hip joint socket. The thread profile of said thread blades is narrowing towards the profile head and tilted in direction to the socket pole, while its point is cut off. Flank angles and head width are identical for all thread blades, while the radial distance of said thread profile from the socket axis is constant only for each single thread blade. Thus, each of said thread blades is surrounded by so called screw surfaces. The thread profile is shown as cut views 145, 146, 147 and 148 positioned at dot and dash lines 141, 142, 143 and 144. For the example shown a vertical right flank angle of 0° was selected, and an inclined left flank angle of 26° (149, 150, 151, 152). Flattened sections of thread blades are drawn as 134 and 135, and the left hand slope as 132, 133. Due to the thread pitch angle, thread blade bottoms are undergoing a height reduction from 153 to 154, as well as from 155 to 156 relative to the socket mantle. The effect of this height reduction from the leading to the trailing portion of the individual thread blades is larger on the polar thread portion than on the equatorial portion of the thread. In the drawing, said height reduction is significantly enlarged for reasons of better understanding. In order to create cutting surfaces 139, 140 and cutting edges 157, 158 on said thread blades, tapping grooves—also called flutes—are applied, indicated by dot and dash lines 136, 137, 138, having an angle with an identical winding direction compared to the thread pitch angle. The tapping groove angle was selected to be about 45°. Thus, the cutting edges are highly "positive", giving guarantee for a soft bone cutting behaviour and low cutting forces. For bringing said behaviour into effect, cutting edges of trailing thread blades have to be exposed relatively to the trailing portion of leading thread blades. Therefore, according to the invention, said thread blades are superimposed by a type of "setting" (an angularly changed or swivelled extension), which in german language is correctly called "Schränkung".

The invention claimed is:

1. A lathing process for non-circular cutting on programmable lathing machines whereby a workpiece is rotated in the chuck of a machine spindle and using a traversable tool at least partial specific non-circular, discontinuous or abruptly changing contours are cut, wherein the turning takes place in jerks, in that the tool is synchronized to the spindle angle and the described contour comprising rounded geometrical transition elements or compound contours is generated by a program comprising jump functions created by linking command blocks with values for selected address parameters such as diameter (X), length (Z), height (Y) and pitch (F) or angle (C), whereby for at least one of these address parameters the program block chain employs a jerk, i.e. a sequence of address parameter values which build into a jump function.

2. Process in accordance with claim 1 wherein the tool is moved relative to the workpiece on a track which can be described as an alternating chain of smoothly flowing and jumping contour elements.

3. Process in accordance with claim 1 wherein the tool is moved relative to the workpiece on a track which only corresponds in a single or in a number of isolated sections with the final contour and in which by way of at least one preceding and/or subsequent machining cycles the superfluous, redundant, undesirable section or section non-compliant with the final contour is remachined to the final contour.

4. Process in accordance with claim 3 wherein the contour on the workpiece is achieved by interleaving at least two machining sequences whereby e.g. in a first sequence the first contour element is machined, and then at least the next contour element is skipped and then a subsequent element is then machined and in at least one additional sequence the skipped contour element or elements are machined and in so doing the previously already machined contour elements are skipped.

5. Process in accordance with claim 3 wherein in each case respectively machined contour sections non-compliant with the final contour are removed or remilled.

6. Process in accordance with claim 1 wherein a driven tool is used in the machining of the contour which has a linear movement of direction in at least one axis.

7. Process in accordance with claim 1 wherein the generation of the contour is achieved exclusively by the movement of the compound rest.

8. Process in accordance with claim 1 wherein a thread program is used.

9. Process in accordance with claim 1 wherein for at least two different address parameters one jerk sequence of address parameter values is used in the program block chain.

10. Process in accordance with claim 1 wherein for at least one of the address parameters the increments formed between the address parameter values of the program block chain are programmed as jerk sequences.

11. Process in accordance with claim 1 wherein the discontinuous contour is generated by the programming of a reciprocal-step process in that the tool is traversed with a sequence of forward and backward movements whereby one of the movements is larger than the other.

12. Process according to claim 1 wherein the program block chain describes a rotationally symmetric contour with a superimposed non-monotonous periodic sequence of increments.

13. Process in accordance with claim 1 for the cutting of discontinuous contour elements which protrude from an angled or curved shell surface whereby the side of the tool predominantly machines the flank of the discontinuous contour element and the tip of the tool predominantly machines the surface shell, wherein the tip of the tool is guided on a track which for the most part runs tangentially to the surface shell and in which the side of the tool is caused by a programmed modification of the tangential traverse speed and/or traverse direction to generate the flank of the discontinuous contour element.

14. Process in accordance with claim 1 wherein the overshoot behavior of the mechanical and/or electronic systems of the lathe or the linear driven tool resulting for the jump commend in the program is directly used for the generation of discontinuous, non-round or abruptly changing contours of crooked contours.

15. Process in accordance with claim 14 wherein the overshoot behavior of the system is used for the direct creation of cutting edges with relief angles on thread segments or blades.

16. Process in accordance with claim 15 wherein the cutting edges are generated by at least partial milling of cutting grooves in the area of a section of the thread blade resulting from the overshoot response of the system and representing the relief angle relict of the overshoot.

17. Application of the process in accordance with claim 1 for the cutting production of special threads on screw-in bodies, e.g. for yielding material such as bone screws, lag screws, vertebral fusion bodies, screws for fixateur externe, screw-in posts for dental implants and screw-in artificial hip joint sockets in particular for the creation of neutral or any pinching or relief angles on the thread blades.

18. Application of the process in accordance with claim 1 for the cutting production screw-in artificial hip joint sockets with any outer contour of the shell surface for example spherical, paraspherical, conical, conical-spherical, parabolic, etc. and a thread on the shell surface which has a profile of the thread teeth with any tooth position, e.g. angled neutrally or towards the pole of the socket and any pitch, e.g. constant or variable pitch, with individual thread blades separated from one another by cutting grooves which create any desired relief angle on at least one of the thread tooth surfaces.

19. Application of the process in accordance with claim 1 for the cutting production of screw-in artificial hip joint sockets with any outer contour of the shell surface for example spherical, paraspherical, conical, conical-spherical, parabolic, etc. and a thread on the shell surface which has a profile of the thread teeth with any tooth position, e.g. angled neutrally or towards the pole of the socket and any pitch, e.g. constant or variable pitch, with individual thread blades separated from one another by cutting grooves which create so-called screw surfaces on at least one of the thread tooth surfaces.

20. Application of the process in accordance with claim 1 for the cutting production of screw-in bodies to create mutual swinging of the thread blades.

21. Process in accordance with claim 1 wherein the non-round or discontinuous contour comprises a closed surface with repeating contour elements.

22. Application of the process in accordance with claim 21 for the production of circular wedge profiles or circular wedge couplings.

* * * * *